(12) United States Patent
Trinh et al.

(10) Patent No.: US 11,116,390 B2
(45) Date of Patent: Sep. 14, 2021

(54) CAPSULE ENTERIC COATING FOR CONTROLLING BALLOON EXPANSION START TIME

(71) Applicant: CAPSOVISION, INC., Saratoga, CA (US)

(72) Inventors: Phat Bao Trinh, San Jose, CA (US); Amy Freitas, Morgan Hill, CA (US); Mikael Trollsas, San Jose, CA (US)

(73) Assignee: CAPSOVISION, INC., Saratoga, CA (US)

(*) Notice: Subject to any disclaimer, the term of this patent is extended or adjusted under 35 U.S.C. 154(b) by 0 days.

(21) Appl. No.: 16/860,028

(22) Filed: Apr. 27, 2020

(65) Prior Publication Data

US 2020/0253462 A1 Aug. 13, 2020

Related U.S. Application Data

(63) Continuation-in-part of application No. 15/647,260, filed on Jul. 12, 2017, now Pat. No. 10,674,899.

(51) Int. Cl.
*A61B 1/04* (2006.01)
*A61B 1/00* (2006.01)
*A61B 1/273* (2006.01)
*A61B 1/06* (2006.01)

(52) U.S. Cl.
CPC ............ *A61B 1/041* (2013.01); *A61B 1/0002* (2013.01); *A61B 1/00006* (2013.01); *A61B 1/0011* (2013.01); *A61B 1/00013* (2013.01); *A61B 1/00016* (2013.01); *A61B 1/00032* (2013.01); *A61B 1/00082* (2013.01); *A61B 1/00156* (2013.01); *A61B 1/0684* (2013.01); *A61B 1/2736* (2013.01)

(58) Field of Classification Search
None
See application file for complete search history.

(56) References Cited

U.S. PATENT DOCUMENTS

| 7,817,354 | B2 | 10/2010 | Wilson |
| 7,983,458 | B2 | 7/2011 | Wang |
| 10,098,526 | B2* | 10/2018 | Trollsas ............ A61B 1/00147 |
| 10,674,899 | B2* | 6/2020 | Trollsas ............... A61B 1/041 |
| 2003/0018280 | A1 | 1/2003 | Lewkowicz et al. |
| 2006/0058829 | A1 | 3/2006 | Sampson et al. |

(Continued)

*Primary Examiner* — Aaron B Fairchild
(74) *Attorney, Agent, or Firm* — Blairtech Solution LLC

(57) ABSTRACT

The present invention discloses a capsule endoscope with specific gravity control. The capsule endoscope comprises a housing to enclose various components, an inflatable device attached to a first longitudinal end of the capsule unit and an enteric coated shell attached to the first longitudinal end of the capsule unit to enclose the inflatable device between the enteric coated shell and the capsule unit. The various components include a camera sub-system for capturing image frames. The inflatable device comprises an inflatable membrane and an effervescent formulation inside the inflatable membrane. The enteric coated shell fits tightly onto the first longitudinal end of the capsule unit to prevent body liquid from leaking into a space between the enteric coated shell and the capsule unit when the capsule unit travels in human gastrointestinal tract after being swallowed.

1 Claim, 5 Drawing Sheets

(56) References Cited

U.S. PATENT DOCUMENTS

| | | | |
|---|---|---|---|
| 2007/0100208 A1* | 5/2007 | Lewkowicz | A61B 1/00082 600/160 |
| 2007/0221233 A1 | 9/2007 | Kawano et al. | |
| 2007/0249900 A1 | 10/2007 | Wilson | |
| 2007/0255098 A1 | 11/2007 | Wang | |
| 2008/0033247 A1 | 2/2008 | Wilson | |
| 2008/0297291 A1 | 12/2008 | Kawano et al. | |

* cited by examiner

|  | Tested Formulations | | | | |
|---|---|---|---|---|---|
| D/ Eudragit™ L30D-55 | 90/10 | 85/15 | 80/20 | 75/25 | 50/50 |
| Separation from capsule | Yes | Yes | Yes | Yes | No |
| Early inflation (2h) | 0.06 ± 0.01 | 0.04 ± 0.01 | 0.06 ± 0.02 | 0.05 ± 0.01 | 0.08 ± 0.02 |
| Clinically | | | | | |
| Cecal release | Slow | n/a | Ok | n/a | Good |
| 12 h, completers | 50% | n/a | 48% | n/a | 63% |

CAPSULE ENTERIC COATING FOR CONTROLLING BALLOON EXPANSION START TIME

CROSS REFERENCE TO RELATED APPLICATIONS

The present invention is a continuation-in-part application of and claims priority to U.S. patent application Ser. No. 15/647,260, filed on Jul. 12, 2017. The present invention is also related to PCT Patent Application, Serial No. PCT/US13/66011, filed on Oct. 22, 2013, PCT Patent Application, Serial No. PCT/US14/68601, filed on Dec. 4, 2014 and U.S. patent application Ser. No. 14/659,832, filed on Mar. 17, 2015. The PCT Patent Applications and U.S. Patent Application are hereby incorporated by reference in their entireties.

FIELD OF THE INVENTION

The present invention relates to diagnostic imaging inside the human body or any other living creature. In particular, the present invention relates to an in-vivo capsule that uses an enteric coating as a means to control specific gravity via controlling design parameters for an inflatable device and an associated enteric coated enclosure.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS sensor array, and transfer the image data as an electrical signal to the proximal end through a cable. Endoscopes allow a physician or a veterinary physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot easily reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia.

An alternative in vivo image sensor that addresses many of these problems is the capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. This patent describes a capsule system using on-board storage such as semiconductor nonvolatile archival memory to store captured images. After the capsule passes from the body, it is retrieved. Capsule housing is opened and the images stored are transferred to a computer workstation for storage and analysis. For capsule images either received through wireless transmission or retrieved from on-board storage, the images will have to be displayed and examined by diagnostician to identify potential anomalies.

FIG. 1 illustrates an exemplary capsule system with on-board storage. The capsule device 110 includes illuminating system 12 and a camera that includes optical system 14 and image sensor 16. A semiconductor nonvolatile archival memory 20 may be provided to allow the images to be stored and later retrieved at a docking station outside the body, after the capsule is recovered. Capsule device 110 includes battery power supply 24 and an output port 26. Capsule device 110 may be propelled through the gastrointestinal (GI) tract by peristalsis.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls (100) on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. Processing module 22 may be used to provide processing required for the system such as image processing and video compression. The processing module may also provide needed system control such as to control the LEDs during image capture operation. The processing module may also be responsible for other functions such as managing image capture and coordinating image retrieval. While FIG. 1 illustrates a capsule endoscope with an archival memory to store captured images, the capsule endoscope may also be equipped with a wireless transmitter to transmit the captures to an external receiver.

After the capsule camera traveled through the GI tract and exits from the body, the capsule camera is retrieved and the images stored in the archival memory are read out through the output port. The received images are usually transferred to a base station for processing and for a diagnostician to examine. The accuracy as well as efficiency of diagnostics is most important. A diagnostician is expected to examine the images and correctly identify any anomaly.

When the capsule device travels through the GI tract, the capsule device will encounter different environments. It is desirable to manage the capsule device to travel at a speed that sufficient sensor data (e.g., images) can be collected at all locations along the portions of the GI tract which are of interest, without wasting battery power and/or data storage by collecting excessive data in some locations. In order to manage the capsule device to travel at a relatively steady speed, techniques have been developed to change the capsule specific gravity during the course of travelling through the GI tract. In some environments, it is desirable to have a capsule with higher specific gravity. In other environments, it may be desirable to have a capsule with lower specific gravity. For example, it is desirable to configure the capsule device to have a lower specific gravity when the capsule device travels through the ascending colon. On the other hand, it may be desirable to configure the capsule device to have a higher specific gravity when the capsule device travels through the stomach or the descending colon, in particular if those anatomies are filled with liquid. However, techniques based on specific gravity or density control may not work reliably due to various reasons. For example, the change of specific gravity or density may not have to take place at the intended section of the GI tract. Therefore, the location of the capsule device inside the GI tract has to be monitored or estimated. However, the location of the capsule device usually cannot be accurately determined without the use of additional equipment outside the patient's body. Therefore, it is desirable to develop reliable means to manage the capsule device to travel at a relatively steady speed in the GI tract.

BRIEF SUMMARY OF THE INVENTION

The present invention discloses a capsule endoscope with specific gravity control. The capsule endoscope comprises a housing to enclose various components, an inflatable device attached to a first longitudinal end of the capsule unit and an enteric coated shell attached to the first longitudinal end of the capsule unit to enclose the inflatable balloon between the enteric coated shell and the capsule unit. The various components include a camera sub-system for capturing image frames. The inflatable device comprises an inflatable balloon and an effervescent formulation inside the inflatable balloon. The enteric coated shell fits tightly onto the first longitudinal end of the capsule unit to prevent body liquid from leaking into a space between the enteric coated shell and the capsule unit when the capsule unit travels in human gastrointestinal tract after being swallowed. The enteric coating on the enteric coated shell prevents or delays body liquid infusion or dissolution of the enteric coated shell when the capsule unit is in stomach. Furthermore, the inflatable device starts to inflate when the enteric coated shell is dissolved and the body liquid enters the inflatable balloon and gets in touch with the effervescent formulation inside the inflatable balloon.

In one embodiment, the enteric coated shell fits tightly onto the first longitudinal end of the capsule unit by only using mechanical fit. Furthermore, a lock ring can be formed in an overlapped section between the enteric coated shell and the first longitudinal end of the capsule unit to cause the mechanical fit.

The shell of the enteric coated shell can be made of hydroxypropyl methylcellulose (HPMC) or gelatin. For example, the shell of the enteric coated shell can be made of HPMC or gelatin by dip coating and a solid HPMC or gelatin piece is later coated with the enteric coating. The enteric coating can be applied to the shell using fluid bed coater, pan coater, dip coater, or any other commonly used coating process.

The enteric coating can be applied to inside and outside of the enteric coated shell. A mixture of Eudragit™ FS 30 D, Eudragit™ L30D-55, any other enteric polymer, or a mixture of any of these can be used for the enteric coating. For example, a ratio of Eudragit™ FS 30 D and Eudragit™ L30D-55 used for the enteric coating is about 90:10, 85:15 or 75:25.

The camera sub-system can be located at or closer to a second longitudinal end of the capsule unit opposite to the first longitudinal end of the capsule unit. In one embodiment, the camera sub-system corresponds to a forward-looking camera located at the second longitudinal end of the capsule unit. In this case, at least one area of the housing at the second longitudinal end of the capsule unit is transparent to allow a field of view of the camera sub-system to pass through said at least one area of the housing. In another embodiment, the camera sub-system corresponds to a panoramic camera located closer to the second longitudinal end of the capsule unit. In this case, at least one area of the housing closer to the second longitudinal end of the capsule unit is transparent to allow a field of view of the camera sub-system to pass through said at least one area of the housing.

The inflatable balloon may comprise polyetherblockamide copolymers, thermoplastic polyurethanes, polyamides, polyamide block copolymers, polyamide elastomers, polyurethanes, polyesters, polyester copolymers, polyamide copolymers, polyurethane copolymers, polyether copolymers, polyesteramides, polyesteramide copolymers, polyvinyl chloride, polyvinyl chloride copolymers, polyvinylidene dichloride, polyvinylidene dichloride copolymers, fluoropolymers, polyvinyl fluoride, polyvinyl fluoride copolymers, polyvinylidene difluoride, polyvinylidene difluoride copolymers, polyvinylpyrrolidone copolymers, or polyvinylalcohol copolymers. The effervescent formulation may comprise bicarbonate salt, anhydrous acid, sodium bicarbonate, potassium bicarbonate, anhydrous citric acid, a mixture of anhydrous sodium bicarbonate and anhydrous citric acid, a mixture of potassium bicarbonate and anhydrous citric acid, a mixture of two or more bicarbonate salts and anhydrous citric acid, or a mixture of bicarbonate and carbonate salts and anhydrous citric acid. Instead of citric acid, alternative crystalline carboxylic acids can be used, ideally multi-functional carboxylic acids. The inflatable balloon is typically sealed with a seal edge but other methods can be used as well.

The specific gravity of the capsule endoscope can be controlled by properly selecting design parameters for the enteric coated shell and the inflatable device. For example, the design parameters can be selected to cause the capsule endoscope to have a specific gravity greater than one when the capsule endoscope is swallowed and when the capsule endoscope stays in stomach. The design parameters can be further selected to cause the capsule endoscope to have the specific gravity less than one when the capsule endoscope reaches ascending colon. Furthermore, the design parameters can be selected to cause the capsule endoscope to have the specific gravity greater than one when the capsule endoscope reaches descending colon.

BRIEF DESCRIPTION OF THE DRAWINGS

FIG. 3 illustrates laboratory test result and clinic evaluation results for different formulations.

DETAILED DESCRIPTION OF THE INVENTION

Figure 1:
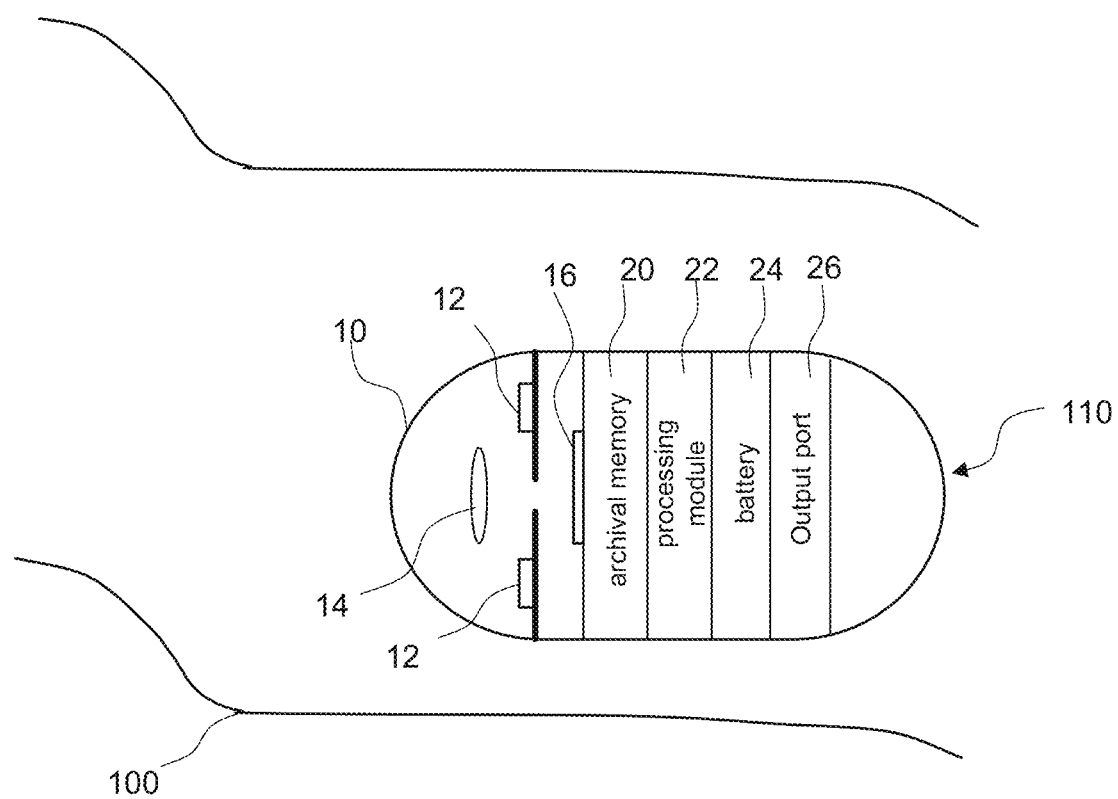
FIG. 1 shows schematically a capsule camera system in the GI tract, where archival memory is used to store captured images to be analyzed and/or examined.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention.

Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

In U.S. Pat. Nos. 7,192,397 and 8,444,554, a capsule device with specific gravity about 1 is disclosed. When the capsule device has a specific gravity about 1, the device will suspend or float in the liquid in the gastrointestinal (GI) track such as in the stomach or in the colon. As disclosed in U.S. Pat. Nos. 7,192,397 and 8,444,554, the capsule device will be carried through the body lumen by a flow of liquid through the body lumen when the capsule device has a specific gravity about 1. However, for an in vivo capsule device, after the capsule device is swallowed by a patient, the capsule device first goes through the pharynx and esophagus into the stomach and the stomach may be filled with liquid. If the specific gravity of the capsule device is less than 1 or the capsule device has a lighter density than the liquid, it will float on the surface of the liquid inside stomach. Thus, it is not conducive for the capsule device to transit through the pylorus into the small bowel. Therefore, it is desirable to cause the specific gravity of the capsule endoscope greater than one when the capsule endoscope is in the stomach.

For a capsule device with an image sensor, it is critical to have a steady and consistent travelling velocity inside different regions of the GI tract, e.g. stomach, small bowel, ascending and descending colons so that smooth and stable images and video can be obtained. The travelling velocity of the capsule camera depends on many factors including regional gastrointestinal motility, gravitational force, buoyancy and viscous drag of the surrounding fluids. After the capsule device is swallowed, it is propelled into the esophagus. Peristaltic waves in the esophagus move the camera into the stomach. After the capsule device passes the cardia and enters the stomach with fluid, the balance among gravitational force, buoyancy and drag from the gastric fluids starts to affect its travelling velocity and transit time. The migrating myoelectric cycle (MMC) can be divided into four phases. Phase 1 lasts between 30 and 60 minutes with rare contractions. Phase 2 lasts between 20 and 40 minutes with intermittent contraction. Phase 3, or housekeeping phase, lasts between 10 and 20 minutes with intense and regular contractions for short period. The housekeeping wave sweeps all the undigested material out of the stomach to the small bowel. Phase 4 lasts between 0 and 5 minutes and occurs between phase 3 and phase 1 of two consecutive cycles. For the capsule device to travel aborally at a desired velocity in all four phases, preferably phases 1 and 2, its specific gravity needs to be greater than 1 (e.g., 1.1) to overcome the buoyance and drag from the surrounding fluid. If phase 3 is detected through image motion detection or accelerometer, the specific gravity can be pushed to a value less than one (e.g., 0.97) for the capsule device to float to the top and to retake the video in a more stable phases.

In the small intestine, BER (basic electrical rhythm) is around 12 cycles per minute in the proximal jejunum and decreases to 8 cycles per minutes in the distal ileum. There are three types of smooth muscle contractions: peristaltic waves, segmentation contractions and tonic contractions. Normally, peristalsis will propel the capsule device towards large intestines. Since the small intestine twists and turns around between the stomach and the large intestine, the capsule device may sometimes be trapped at corners and turns. In this case, motion detection may be used to detect such situation. Accordingly, density-changing mechanisms can be used to slightly change the balance between gravity and buoyancy so that the capsule device can leave the trap sooner before the next peristalsis.

While the large intestine is one organ, it demonstrates regional differences. The proximal (ascending) colon serves as a reservoir and the distal (transverse and descending) colon mainly performs as a conduit. The character of the luminal contents impacts the transit time. Liquid passes through the ascending colon quickly, but remains within the transverse colon for a long period of time. In contrast, a solid meal is retained by the cecum and ascending colon for longer periods than a liquid diet. In the ascending colon, retrograde movements are normal and occur frequently. In order for the buoyant force to overcome the gravitational force and retropulsion, the specific gravity of the capsule device according to an embodiment of the present invention is decreased to less than less than one (e.g., 0.99 or less) after the capsule enters the ascending colon. Alternatively, the density of the capsule device as a whole has lighter density than the surrounding fluid. In the descending colon and rectum, propulsive contractions prevail. The capsule device is carried aborally towards the rectum by the natural propulsion. However, increasing the specific gravity of the apparatus to larger than one (e.g., 1.1 or larger) can shorten the transit time and allow a smooth and steady motion. Therefore, it is desirable to cause the specific gravity to be greater than one when the capsule endoscope reaches the descending colon.

In order to properly set the specific gravity or the density of the capsule device, it needs to know which regions of the GI track that the capsule device is located. There are various know region detection methods in the literature. The region detection methods include estimated transit time (e.g., about 1 hour in stomach and about 3-4 hours in small bowel), identification of image contents based on captured images by the capsule device, motion detection based on the captured images by the capsule device, pH detection (pH value increasing progressively from the stomach (1.5-3.5) and the small bowel (5.5-6.8) to the colon (6.4-7.4), pressure sensor (higher luminal pressure from peristaltic motion in the colon than that in the small bowel) and colonic microflora. The ascending colon has a larger diameter than other regions besides the stomach. The size may be detected by the methods disclosed in U.S. Patent Publications, Series No. 2007/0255098, published on Nov. 1, 2007, U.S. Patent Publications, Series No. 2008/0033247 published on Feb. 7, 2008 and U.S. Patent Publications, Series No. 2007/0249900, published on Oct. 25, 2007.

Accordingly, in PCT Patent Application, Serial No. PCT/US13/66011, a method is disclosed to configure the capsule device to have a specific gravity (SG) larger than 1 or a density higher than the liquid in the stomach when the capsule device is in the stomach. After the capsule passes through the small bowel and enters the cecum, it has to transit through the ascending colon. PCT Patent Application, Serial No. PCT/US13/66011 further discloses a method to cause the capsule device to have a specific gravity less than 1 or to have a lighter density than the liquid in the cecum and ascending colon.

In order to control the SG, PCT Patent Application, Serial No. PCT/US13/66011 discloses a capsule with an inflatable balloon, which is a deformable membrane, containing effervescent material. The inflatable balloon is expandable and made of material that is permeable to external fluid, such as water or gastric juice. Furthermore, an enteric coating is applied to the outer surface of the inflatable balloon. The enteric coating may also cover the entire capsule system. Furthermore, instead of coating the balloon, the balloon may be put into a capsule shell, which will dissolve in the stomach or small bowel within about 30 minutes of swallowing, unless the capsule shell is enteric or coated with an enteric, in which case it will not dissolve in the low pH of the stomach, but disintegrate in the higher pH environment of the small bowel or colon. When the capsule device approaches the terminal ileum or the cecum, the enteric coating will dissolve due to the higher pH level. With the enteric coating dissolved, external fluid will gradually get into the deformable member. When the fluid makes contact with the effervescent formulation, gas will be generated to expand the deformable member. While a small amount of fluid gets into the deformable member, the gas generated is able to expand the deformable member so that the capsule device as a whole has a specific gravity less than one.

The effervescent material should be in contact with the semipermeable membrane of the deformable member so that water that diffuses through the membrane will reach the effervescent material as designed. The effervescent material may be a powder or dispersion that coats a portion of the inside surface of the membrane or it might comprise granules that rest on the surface of the membrane.

For controlling the specific gravity of the capsule device, an inflatable device (e.g. a balloon containing effervescent materials) is often used. The inflatable balloon usually is attached to the capsule. An enteric coating is applied to the outer surface of the inflatable shell to delay the time to inflate until the capsule reaches or about to reach an intended anatomic location (e.g. after leaving the stomach). The enteric coating may be applied to the whole capsule device or the capsule can be enclosed using an enteric shell according to the conventional approach. When the enteric coating is applied to the whole capsule device, it will cover the clear window of the camera sub-system on the capsule housing. After the enteric coating dissolves, the inflatable balloon will inflate when the body liquid enters the membrane (i.e., the shell) and gets in touch with the effervescent formulation. However, the residual left over on the capsule housing from the enteric coating may reduce the transparency of the clear window on the capsule housing. Accordingly, it will reduce image quality. On the other hand, when a capsule shell is used, the overall capsule size with the capsule shell may become noticeably larger than the capsule device without the capsule shell. The size increase will make the swallowing a little harder. Furthermore, the use of capsule shell may increase the overall cost.

Accordingly, the present invention discloses a different structure and process to apply enteric coating to the capsule device. When a forward-looking camera is used, the camera usually is located at one longitudinal end of the capsule device. When a panoramic camera sub-system is used, such as the panoramic imaging system disclosed in U.S. Pat. No. 7,817,354, the camera sub-system including multiple lens modules is usually located near one longitudinal end while the battery is located near another longitudinal end. Accordingly, the present invention discloses the use of an enteric coated shell to cover the inflatable device. The inflatable device is affixed to one longitudinal end of the capsule device opposite from the camera end. The enteric coated shell is then attached to the end of the capsule with the inflatable device attached. The enteric coated shell should provide a tightly fitted or sealed environment for the inflatable device to prevent liquid from unintentionally leaking into the space between the enteric coated shell and the end of the capsule with the inflatable device attached.

After the capsule device with the enteric coated shell on is swallowed by a human subject, it will go down to the stomach. Due to the enteric coating, the shell can sustain the acid environment in the stomach for a period of time without letting liquid to get into inside of the shell. After the capsule leaves the stomach, the environment becomes less acid and the enteric coating will start to dissolve. By properly selecting design parameters for the enteric coated shell (e.g. the enteric coating chemicals, the materials for the shell structure, etc.) and the inflatable device (e.g. the size, material and thickness of the inflatable balloon, the effervescent material and amount, etc.), it is expected to have the inflatable device sufficiently inflated and to have the capsule become buoyant when the capsule device reaches a target anatomic location, such as the ascending colon.

Figure 2A:
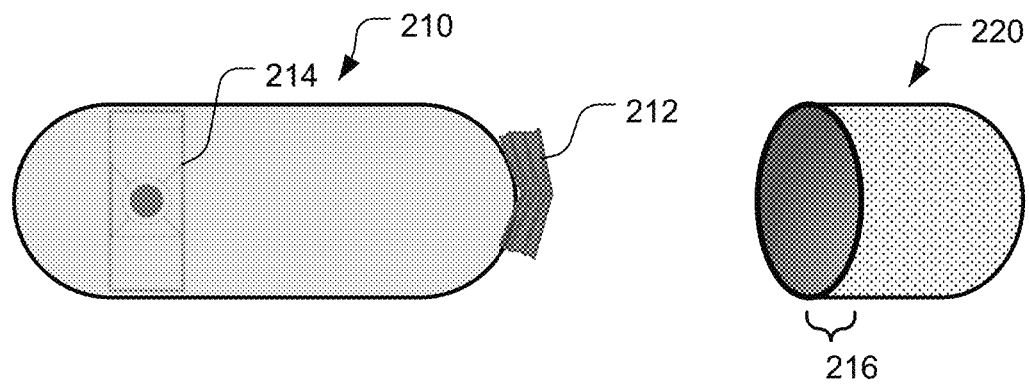
FIG. 2A illustrates an example of specific gravity control according to an embodiment of the present invention, where an inflatable attachment is affixed to one longitudinal end of the capsule opposite to the end where the camera is closer to and an enteric coated shell is used to enclose the inflatable device.

FIG. 2A illustrates an example of capsule device with specific gravity control according to an embodiment of the present invention, where an inflatable device 212 is affixed to one longitudinal end of the capsule 210 opposite to the end where the camera 214 is closer to. The enteric coated shell 220 has a shape closely matched with the shape of the inflatable-device attached end of the capsule 220 or at least a section of the shell near the opening 216 closely matched with a corresponding section of the inflatable-device attached end of the capsule 220. According to one embodiment, the exterior of the shell is coated with an enteric material. Since the enteric coated shell 220 has a shape closely matched with the shape of the inflatable-attachment end of the capsule 220 or at least a section of the shell near the opening 216 closely matched with the corresponding section of the inflatable-device attached end of the capsule 220, a section of the capsule toward the inflatable-device attached end will tightly fit into the shell when the shell is placed onto the inflatable-device attached end of the capsule.

The terms of inflatable balloon and deformable balloon have been used interchangeably in this disclosure. The material for the inflatable balloon should be carefully selected. While the inflatable balloon is expandable when gas is generated, the balloon should be a type of membrane to allow body liquid to diffuse into the shell so that gas can be generated due to combination of water and effervescent formulation. Furthermore, the membrane should allow the gas to leak gradually so that the inflatable shell can deflate after a specific period of time so that the capsule with the inflatable device attached will not be trapped in the gastrointestinal tract. The inflatable balloon may comprise polyetherblockamide copolymers, thermoplastic polyurethanes, polyamides, polyamide block copolymers, polyamide elastomers, polyurethanes, polyesters, polyester copolymers, polyamide copolymers, polyurethane copolymers, polyether copolymers, polyesteramides, polyesteramide copolymers, polyvinyl chloride, polyvinyl chloride copolymers, polyvinylidene dichloride, polyvinylidene dichloride copolymers, fluoropolymers, polyvinyl fluoride, polyvinyl fluoride copolymers, polyvinylidene difluoride, polyvinylidene difluoride copolymers, polyvinylpyrrolidone copolymers, or polyvinylalcohol copolymers. The inflatable balloon is typically sealed with a seal edge but other methods can be used as well.

Figure 2B:
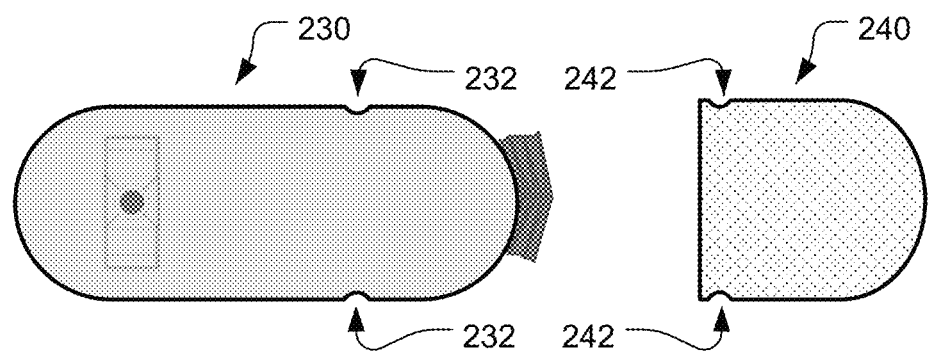
FIG. 2B illustrates an example of fitting the enteric coated shell onto the inflatable-device attached end of the capsule using only mechanical fit according to an embodiment of the present invention.

The shell can be made of hydroxypropyl methylcellulose (HPMC) or gelatin by various known methods such as dip coating. The solid HPMC or gelatin pieces are later coated with Eudragit™ (trademark of Rohm GmbH & Co. KG. Darmstadt in Germany) formulations or similar enteric coating formulations using either fluid bed coater, pan coater, or through dip coating. As is known in the field, HPMC is a water soluble polymer that can be used in solution. Also, HPMC can be used to create a solid plastic material that later can be dissolved in water, if the temperature is right. However, non-functionalized HPMC does not contain any carboxylic acid functional groups and therefore does not have intrinsic enteric properties. In one embodiment of the present invention, the coated HPMC capsule is placed to the camera capsule strictly by mechanical fit. For example, a lock ring (e.g. an area with slightly smaller inner diameter) can be used that makes the fit tight. FIG. 2B illustrates an example of fitting the enteric coated shell onto the inflatable-device attached end of the capsule using a lock ring according to an embodiment of the present invention. In this example, a ring 242 with a smaller diameter is formed near the open edge of the shell 240. On the other hand, a mating grove ring 232 on the housing of the capsule 230 is formed. The shell 240 and the capsule 230 can be assembled by pushing the two parts toward each other so that the shell becomes locked onto the capsule (250). While HPMC and gelatin are used as examples to form the shell, other water-soluble materials may also be used.

On the other hand, there are various effervescent materials that can be used to generate gas upon combination with water. The effervescent formulation may comprise bicarbonate salt, anhydrous acid, sodium bicarbonate, potassium bicarbonate, anhydrous citric acid, a mixture of anhydrous sodium bicarbonate and anhydrous citric acid, a mixture of potassium bicarbonate and anhydrous citric acid, a mixture of two or more bicarbonate salts and anhydrous citric acid, or a mixture of bicarbonate and carbonate salts and anhydrous citric acid. Instead of citric acid, alternative crystalline carboxylic acids can be used, ideally multi-functional carboxylic acids.

In order to add assurance to have tight seal at the joint (e.g., joint 410 in FIG. 4) between a section of the shell 220 and a section of the inflatable-device attached end of the capsule 210, adhesive or glue can be applied to exterior side of the capsule, the inside of the shell or both at the joint.

Various grades of Eudragit™ can be selected as the enteric materials to coat on the HPMC. For example, in one embodiment, a mixture of Eudragit™ FS 30 D and Eudragit™ L30D-55 is used. The preferred mixtures are about 90%:10%, 85%:15%, 75%:25% and about 50%:50% depending on what effervescent material and balloon thickness are used. Furthermore, various plasticizers can be used in the formulation to ensure good mechanical properties of the coating so that it does not fracture during the assembly process. Also, cares have to be taken to avoid reducing the glass transition temperature of the formulation too much and to ensure good shelf-life properties. The choice of Eudragit™ grades (e.g. Eudragit™ FS 30D and Eudragit™ L30D-55) may be dependent on the desired time or anatomic locations (e.g. duodenum, jejunum, ileum or ascending colon) for the enteric coating to become fully dissolved or mostly dissolved. The enteric coating may also be made of polymers, polysaccharides, plasticizers, methyl cellulose, gelatin, sugar, or other materials. Hydroxypropylcellulose, hypromellose acetate succinate and methacrylic acid co-polymer type C are examples of other enteric polymers.

FIG. 3 illustrates laboratory test result and clinic evaluation results for different formulations. In the laboratory test, whether the enteric shell will be separated from the capsule at a specified time (e.g., expected time of excretion) is checked. As shown in FIG. 3, among various formulations, the enteric-coated shell with an about 50:50 formulation will not cause separation. On the other hand, other formulations evaluated will cause the shell to separate. While separation from the capsule may not be an issue, it is preferred not to have the balloon separated from the capsule since it is more likely that the balloon will not be prematurely inflated. Another factor evaluated is the early inflation at 2 hours into the stomach environment. The enteric coating is expected not to dissolve in the less acid stomach environment. Therefore, the balloon is not expected to inflate. All formulations seem to work well. In the clinical evaluation, cecal release is evaluated. The about 50:50 formation has good chance of cecal release in the clinical evaluation. Another factor evaluated is the completion rate within 12 hours (i.e., capsule excretion within 12 hours). The about 50:50 formulation has noticeable better completion rate than other formulations.

Figure 4:
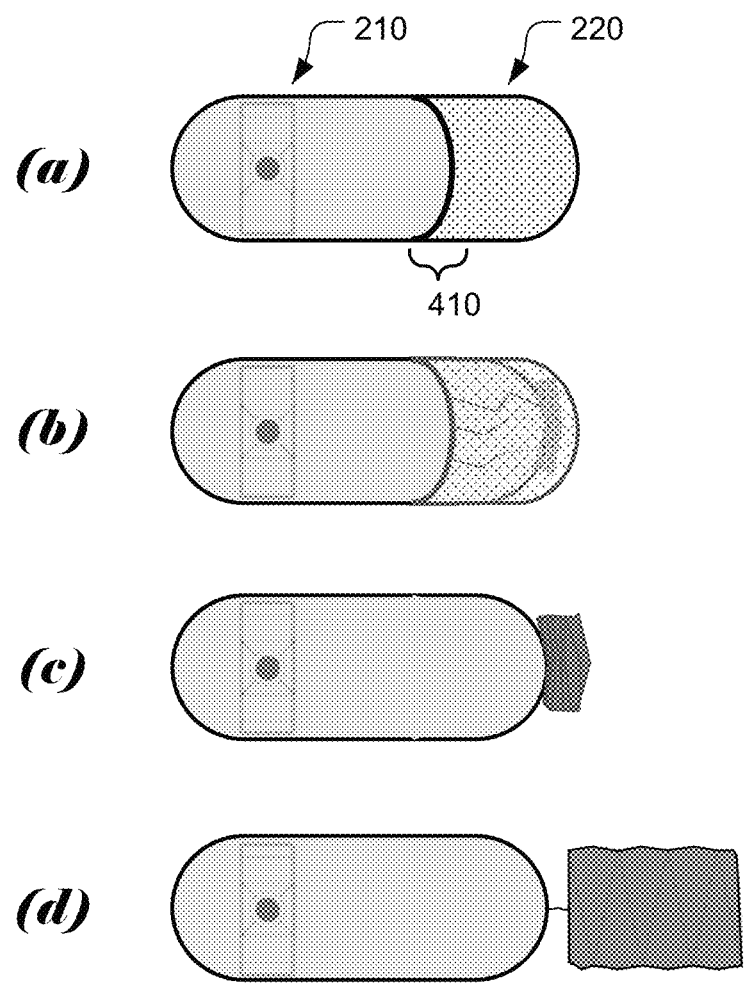
FIG. 4 illustrates an example of various states of the capsule incorporating an embodiment of the present invention.

FIG. 4 illustrates an example of various states of the capsule incorporating an embodiment of the present invention. In state (a), the shell 220 is placed at the inflatable-device end of the capsule 210. At least, a section 410 at the open end of the shell fits the capsule 210 tightly to prevent or delay water from leaking into the area between the capsule 210 and the shell 220. The capsule with the shell will stay in this state at the time when it is swallowed, travels through the esophagus and stays in the stomach. The coating prevents and delays water infusion and dissolution of the capsule at acid stomach environment with pH values at about 1.5 to 3.5. Once the capsule leaves the stomach and enters the small bowels, the pH is increased to around (e.g. pH 6), the acidic groups are deprotonated and replaced by sodium and/or potassium ions, which makes the enteric polymers water soluble. Once this happens the HPMC is no longer protected and it will begin to dissolve or swell as shown in state (b). Soon, the shell transition will allow the inflatable device (e.g. balloon) to be exposed to body liquid as shown in state (c). The inflatable device comprises a deformable member (e.g. a balloon) with effervescent material inside. The inflatable balloon is typically sealed with a seal edge but other methods can be used as well. The membrane is permeable to external fluid, such as the water of the intestinal fluids. The effervescent chemicals in the inflatable shell will generate gas when the chemicals are combined with water. The gas generated will inflate the deformable member to render the density of the capsule device as a whole substantially less than 1. The capsule with the inflatable device fully or mostly inflated is shown as state (d).

The inflatable device will later deflate as the gas in the deformable shell diffuses out of the deformable shell. In this case, the capsule device will have a specific gravity greater than one again. Furthermore, the reduced volume of the inflatable device will reduce the risk of being trapped inside the GI tract if an obstruction such as a tumor exists.

Figure 2B:
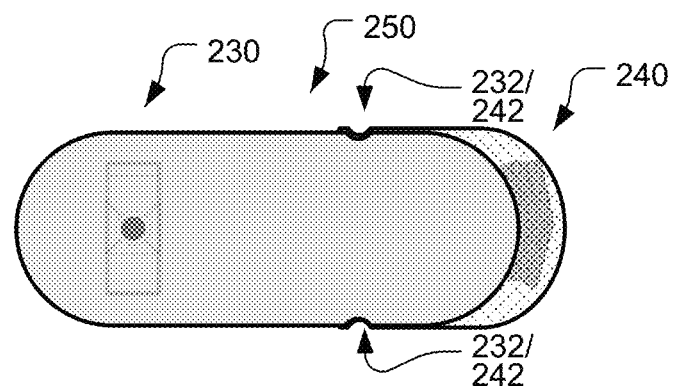
Figure 5:
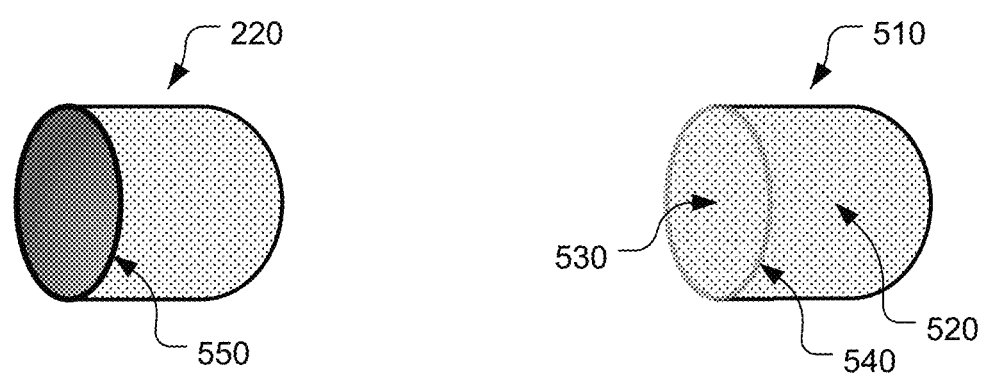
FIG. 5 illustrates an example of an enteric coated shell in various states according to an embodiment of the present invention, where both the inside and the outside of the shell are enteric coated.

For the shell 220 illustrated in FIG. 2, the enteric coating is only applied to the exterior of the shell. The edge 550 of the shell may not be fully covered by the enteric coating as shown in FIG. 5. Therefore, when the capsule with the shell attached is exposed to the acid environment (e.g. stomach), the uncovered edge of the shell may become a weak point for the shell to start swelling and dissolving immaturely. Accordingly, in another embodiment, the shell is enteric coated on both the outside and the inside. For example, the whole shell can be dipped into an enteric coating bed, or spray coated, to be fully coated. In this case, the edge of the shell 510 can be fully covered by the enteric coating as shown in FIG. 5, where the outside 520, inside 530 and the edge 540 are all covered by enteric coating. The shell with double-side enteric coated will work more reliably than the just exterior coated shell.

Figure 6A:
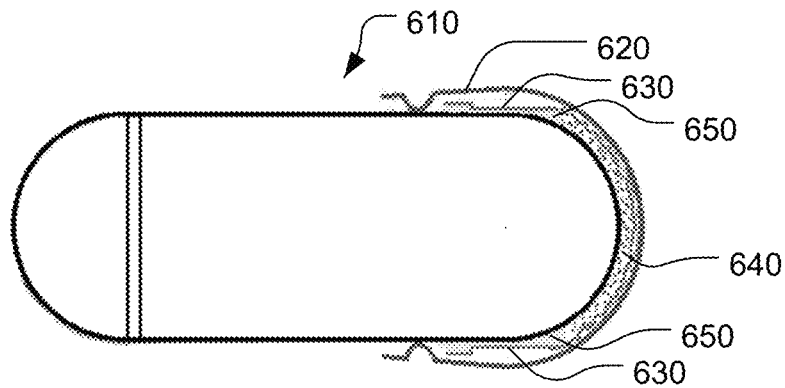
FIG. 6A illustrates an initial state of another capsule design incorporating an inflatable-device with an enteric coated shell, where the inflatable-device comprises an expandable membrane glued to one end of the capsule.
Figure 6B:
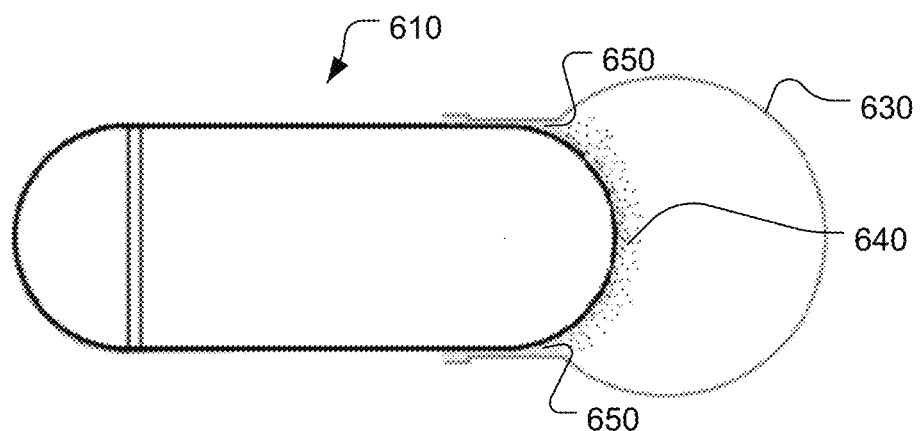
FIG. 6B illustrates an inflated state of the capsule design of FIG. 5A.
Figure 6C:
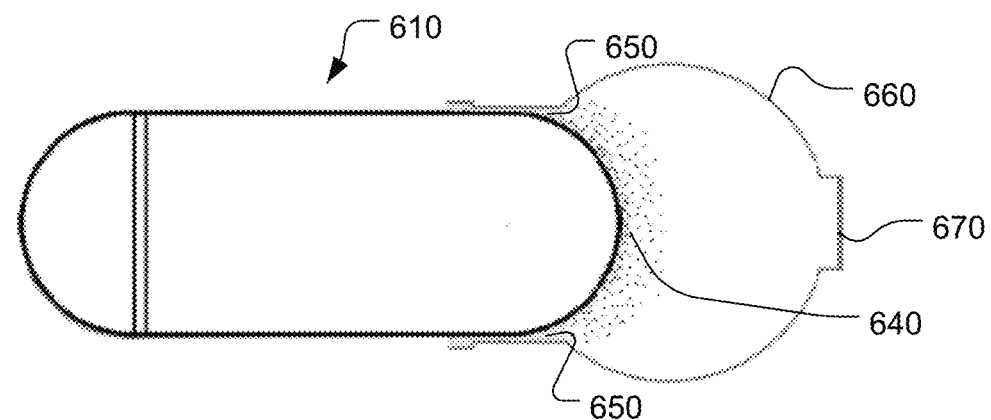
FIG. 6C illustrates an inflated state of yet another capsule design similar to FIG. 5A except that the inflatable device has a seal edge.

FIG. 6A illustrates an initial state of another capsule design 610 incorporating an inflatable-device 630 with an enteric coated shell 620, where the inflatable-device comprises an expandable membrane 630 attached to one end of the capsule using an adhesive 650. Effervescent formulation 640 is enclosed by the expandable membrane. The capsule device is designed to have a special gravity greater than one in the initial state. After the capsule travels to a less acidic environment, after some time the shell will swell or dissolve and allow the inflatable device to be exposed to body liquid. The effervescent material inside the expandable membrane will become substantially inflated as shown in FIG. 6B to cause the specific gravity less than one. FIG. 6C illustrates an inflated state of yet another capsule design similar to FIG. 6A except that the inflatable device has a seal edge 670 in the expandable membrane 670.

The capsule device with the specific gravity control according to embodiments of the present invention is able to achieve a density heavier than the body lumen liquid in one region of the GI tract (e.g. the stomach) and then has a density lighter than the body lumen liquid in another region of the GI track (e.g., the cecum or ascending colon). Furthermore, the capsule may have a specific gravity greater than one again after an extended period of time when the gas generated leaks out and more liquid enters the inflatable shell.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A capsule endoscope with specific gravity control, comprising:
  a capsule unit comprising:
    a battery;
    a light source;
    a camera sub-system for capturing image frames of a scene illuminated by the light source;
    a housing adapted to be swallowed, wherein the battery, the light source and the camera sub-system are enclosed in the housing;
  an inflatable device attached to a first longitudinal end of the capsule unit, wherein the inflatable device comprises an inflatable balloon and an effervescent formulation inside the inflatable balloon; and
  an enteric coated shell attached to the first longitudinal end of the capsule unit to enclose the inflatable device between the enteric coated shell and the capsule unit; and
  wherein a 50:50 ratio of Eudragit™ FS 30 D and Eudragit™ L30D-55 is used for enteric coating on the enteric coated shell to prevent or delay body liquid infusion or dissolution of the enteric coated shell when the capsule unit is in stomach; and
  wherein the inflatable device starts to inflate when the enteric coated shell is dissolved and the body liquid enters the inflatable balloon and gets in touch with the effervescent formulation inside the inflatable balloon.

* * * * *